United States Patent [19]

Choustoulakis

[11] 4,415,797

[45] Nov. 15, 1983

[54] APPARATUS FOR DISPENSING A MATERIAL INTO THE ATMOSPHERE

[76] Inventor: Nikitas Choustoulakis, 181 Imittou St., Athens 502, Greece

[21] Appl. No.: 254,564

[22] Filed: Apr. 15, 1981

[30] Foreign Application Priority Data

Apr. 19, 1980 [GR] Greece ................................. 61716

[51] Int. Cl.³ .............................................. B05B 1/24
[52] U.S. Cl. .................................... 219/273; 222/644; 222/646; 219/271; 219/275; 239/136; 239/70
[58] Field of Search ............... 219/271, 272, 273, 274, 219/275, 276; 239/13, 67, 70, 133, 134, 135, 136, 337; 261/142; 222/146 HA, 638, 641, 644, 645, 646, 649, 647; 43/129, 130; 252/67; 128/203.27, 200.14

[56] References Cited

U.S. PATENT DOCUMENTS

| | | | |
|---|---|---|---|
| 1,683,760 | 10/1928 | Conners | 219/273 |
| 2,615,215 | 10/1952 | Stagner | 219/273 |
| 2,662,332 | 12/1953 | McIntire | 219/273 |
| 2,736,987 | 2/1956 | Tomasovich | 43/129 |
| 2,758,412 | 4/1956 | Loibl | 219/273 |
| 3,134,191 | 5/1964 | Davis | 222/146 HA |
| 3,187,949 | 6/1965 | Mangel | 222/70 |
| 3,675,360 | 7/1972 | Pierce | 43/129 |
| 3,739,144 | 6/1973 | Janson | 219/362 |
| 3,851,146 | 11/1974 | Bennett | 219/300 |
| 3,869,815 | 3/1975 | Bullock | 219/273 |
| 3,974,941 | 8/1976 | Mettler | 222/70 |
| 4,171,754 | 10/1979 | Rosado | 222/70 |
| 4,198,574 | 4/1980 | Price et al. | 307/97 |

FOREIGN PATENT DOCUMENTS 1123923  8/1968  United Kingdom .

Primary Examiner—B. A. Reynolds
Assistant Examiner—Teresa J. Walberg
Attorney, Agent, or Firm—Sughrue, Mion, Zinn, Macpeak, and Seas

[57] ABSTRACT

A pressurized can (3) containing material to be dispensed by evaporation is inserted into a case (1) and secured therein by latches (16). An actuator assembly comprises an annular solenoid (21,22) surrounding a plunger (28). The plunger (28) has an axial bore for receiving a shaft tube (29) which is pressed by plunger (28) on a can valve when the solenoid (21,22) is energized. The shaft tube (29) is provided with a nozzle tube (31) extending toward the opening (37) of an annular electrical heating device (34) comprising a perforated disk (39). Material from the can (3) is released by energizing the solenoid (21,22) automatically at selectable time intervals for preset durations. The material falls on the heated perforated disk (39) and evaporates through the holes (40) in the disk (39) into the atmosphere. Higher amounts of insecticide, deodorant and disinfectant agents can be automatically evaporated into a space of higher volume with less material by this apparatus.

12 Claims, 8 Drawing Figures

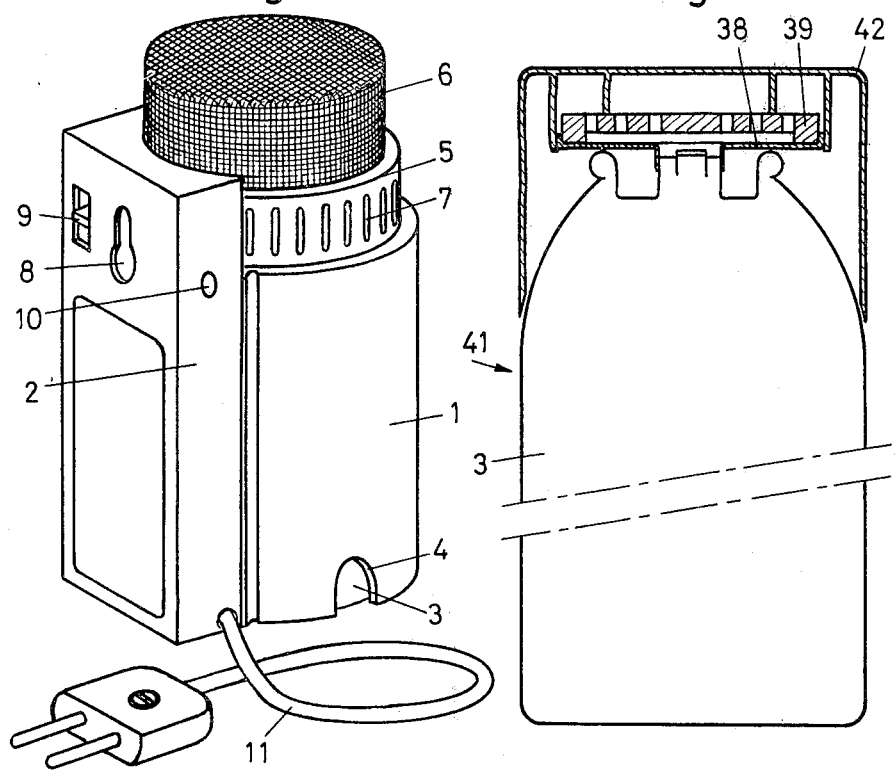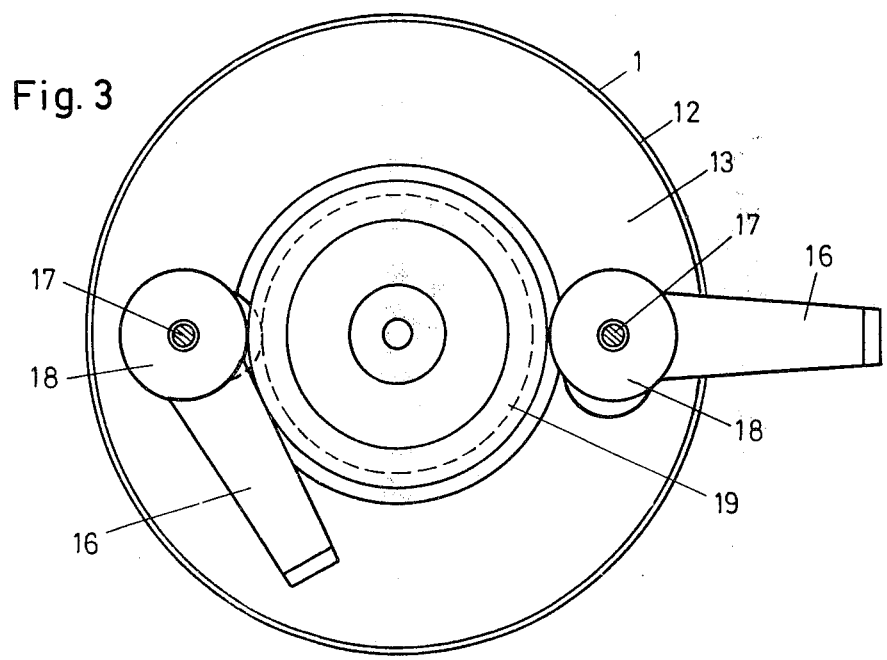

APPARATUS FOR DISPENSING A MATERIAL INTO THE ATMOSPHERE

BACKGROUND OF THE INVENTION

This invention is concerned with an apparatus for dispensing a material into the atmosphere. More particularly, the invention relates to such an apparatus which electrically dispenses by evaporation an insecticide, a deodorant, a smoke consumer or a similar material into the surrounding atmosphere at selectable time intervals.

Known electric devices for the evaporation of insecticides or deodorants comprise an electrically heated element on which the material to be evaporated is placed in solid form. The material may have the form of a piece of cellulose impregnated with the insecticide or the deodorant. Due to the heating effect, the insecticide or deodorant evaporates from the cellulose within a definite period of time. If further insecticide or deodorant is to be evaporated into the surrounding atmosphere, a fresh quantity of impregnated cellulose has to be placed on the heating element.

The known devices show the disadvantage that they dispense the insecticide or deodorant only within a restricted space around the device. If a larger volume of atmosphere has to be treated with the insecticide or deodorant, several similar devices have to be used. Moreover, as the evaporated insecticides or deodorants contain components which form deposits on the heating element, such deposits must be regularly removed from the heating element. Therefore, the known devices do not allow a continuous and controlled operation without constant attention.

SUMMARY OF THE INVENTION

It is a principal object of the invention to disclose an apparatus of the kind referred to above which at selectable time intervals automatically disperses by evaporation a controlled amount of the material to be dispensed into the whole surrounding space.

It is a further object of the invention to disclose an electric and electronic actuation and control system for a dispenser of a material contained in a reservoir.

It is a still further object of the invention to disclose a package comprising a container for a material to be dispensed, which removes the necessity of repeated cleaning of a heating element in a dispensing apparatus to be provided with the container.

These and further objects are achieved by the present invention, specific embodiments of which, by way of example, are explained in the following description and represented in the attached drawings.

BRIEF DESCRIPTION OF THE DRAWINGS

FIG. 1 shows a perspective view of the exterior of an embodiment of the apparatus according to the present invention.

FIG. 3 shows a top view of a mechanism holding in place a can containing material under pressure to be dispensed by the apparatus of FIG. 1.

FIG. 4 shows a view of a selling package comprising the can containing material under pressure to be dispensed by the apparatus of FIG. 5.

DESCRIPTION OF THE PREFERRED EMBODIMENTS

Figure 2:
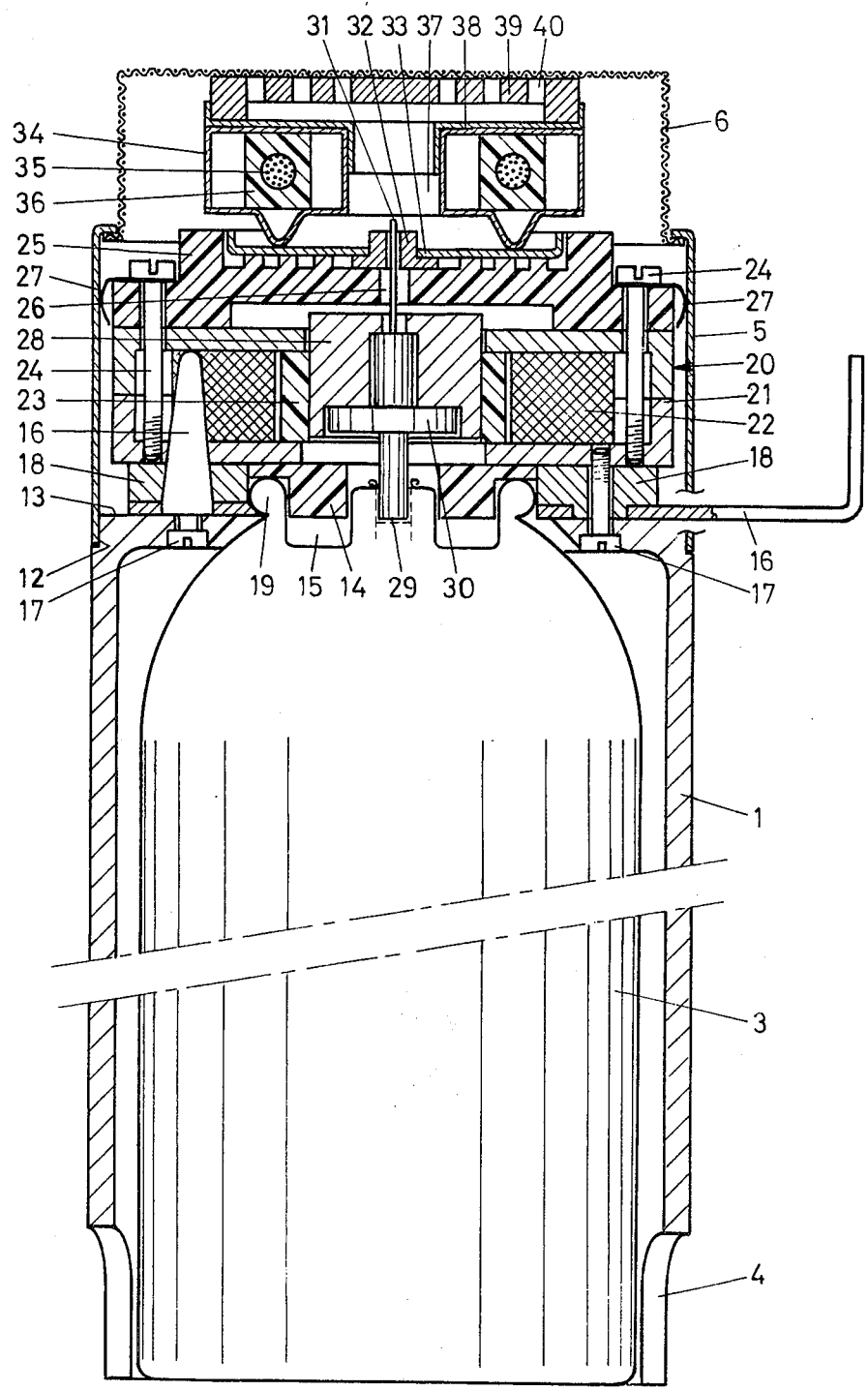
FIG. 2 shows a longitudinal cross section of the embodiment of FIG. 1.

The dispensing apparatus represented in FIG. 1 has a main body including a substantially cylindrical case 1 and a substantially rectangular box 2 which is attached to case 1 or forms part thereof, both case 1 and box 2 being made from a plastic material. Case 1 contains a pressurized can 3 which is filled with a material to be dispensed by the apparatus. Can 3 is held in case 1 by a fastener assembly described below with reference to FIGS. 2 and 3, and may be removed from case 1 through the open bottom side of the case when all material in the can has been dispensed. A fresh replacement can 3 may then be inserted through the bottom of case 1. Openings 4 in the cylindrical wall of case 1 at its bottom facilitate the removal of can 3 from case 1, and form an inlet for air when the apparatus is placed on a flat surface. In addition to the can fastener assembly mentioned above, further assemblies are bolted to case 1, i.e. a valve actuator assembly and a heating assembly, which all will be described below with reference to FIG. 2. These assemblies are covered by a top cap 5 which engages the upper edge of case 1, and which is provided with and holds a stainless steel wire screen 6. Top cap 5 also has ventilation slits 7 on its cylindrical side face.

Rectangular box 2 contains an electronic control circuit for actuating the apparatus, i.e., for dispensing a controlled amount of the material in can 3 to the surrounding atmosphere within controlled time intervals. Rectangular box 2 has an elongated hole 8 at its back cover for wall mounting of the apparatus, and a time interval selector switch 9. A side face of rectangular box 2 is provided with a pilot lamp 10 indicating the operative state of the apparatus. The present apparatus is connected to an a.c. mains supply by means of a power supply cord 11. Typically, the apparatus may be adapted for use on a 220 volts, 50 Hz or on a 110 volts, 60 Hz mains supply.

Referring now to FIG. 2, case 1 with the bottom openings 4 is represented in a sectional view. Top cap 5 provided with wire screen 6 is put in a circular recess 12 at the top edge of case 1. Pressurized can 3 is inserted into the cylindrical hollow space of case 1 with its convergent top passing through a circular opening in the top face 13 of case 1. An annular can guide 14 which engages a corresponding annular groove 15 of can 3, and which is made of a thermal insulation material, serves the purposes of both ensuring a co-axial position of can 3 inserted in case 1, and providing a thermal protection of can 3 with respect to upperlying elements described below. Two latches 16 are pivotally held on top face 13 of case 1 by respective screws 17 which also attach the upperlying elements to case 1 over intermediate bushings 18. A top view of latches 16 is represented in FIG. 3. From FIGS. 2 and 3, it can be seen that can 3 is firmly held in place by the latches 16 when they are in their inwardly turned position shown on the left side of FIG. 2 and in FIG. 3, the free ends of the latches engaging an annular groove below a rounded projecting edge 19 of can 3. When the latches 16 are rotated into their outer positions as shown on the right side of FIG. 2 and as indicated by arrows in FIG. 3, can 3 is freed to be removed (or inserted) without obstacle.

A valve actuator assembly 20 comprises an annular solenoid including a solenoid core 21, composed of two identical half-portions, an annular solenoid coil 22 placed within the half-portions of the solenoid core 21, and a guide sleeve 23 at the inner diameter of solenoid core 21 and solenoid coil 22. The solenoid is held together by means of screws 24, and attached to the top face of case 1 by means of screws 17 which pivotally hold the latches 16. Screws 24 also hold an upper heat insulating plate 25 which covers the upper face of the solenoid, and which may be made of a synthetic resin plastic or a ceramic material. Heat insulating plate 25 has a central hole 26 coaxially aligned with the central opening of guide sleeve 23. Moreover, bent sleeve type springs 27 are clamped on plate 25 to hold top cap 5 in place.

A plunger 28 made of a magnetic material is placed into the circular opening of guide sleeve 23. Plunger 28 has an axial bore receiving an axial shaft tube 29, and a recess receiving a disk 30 fixed to tube 29. The lower end of shaft tube 29 extends into an opening of can 3 beneath which can 3, as known, is fitted with a valve (not shown). The upper end of shaft tube 29 is provided with a nozzle tube 31 which extends through the central bore in heat insulating plate 25, and is guided therein by a bushing 32 made of a plastic material such as "Teflon". Both plunger 28 and shaft tube 29 are movable in an axial direction. The lower end of shaft tube 29 rests on the valve (not shown) in can 3. Disk 30, on which plunger 28 then rests, is so attached to shaft tube 29 in a longitudinal position that the mean horizontal plane of plunger 28 is located higher than the mean horizontal plane of solenoid core 21. Therefore, upon actuation of the solenoid, i.e. electric excitation of its coil 22, the plunger 28 will be drawn downwardly, thus pushing the shaft tube 29 downwardly which then opens the valve of can 3.

A metal plate 33 placed on the upper corrugated face of heat insulating plate 25 serves as a support for a metallic annular heating device 34, spacers 35 between metal plate 33 and heating device 34 effectuating a further heat insulation. Heating device 34 comprises at least one inner heater element 35 of the type having electric resistance which is conveniently insulated by a surrounding insulation material 36, e.g., a ceramic material. Heating device 34 has an axial opening 37 coaxially aligned with nozzle tube 31. A metallic plate 38 having a ring-shaped area resting on heating device 34, a sleeve-shaped protrusion extending into opening 37, and a peripheral rim holds a metallic disk 39 which is provided with holes 40. Both plate 38 and disk 39 are removable by simply lifting them off upwardly. They are retained in place and prevented from falling out when the apparatus should be turned with its top downwardly, by the metallic screen 6 attached to top cap 5.

The operation of the apparatus according to FIGS. 1 and 2 is as follows. On each command from the electronic control circuit in box 2, the output of which is connected to solenoid coil 22 by appropriate conductors (not shown), solenoid coil 22 is energized and thus moves plunger 28 downwardly. Plunger 28 drives shaft tube 29 which urges the valve in can 3 downwardly to open for a time period which is preset in the electronic control circuit in box 2. While the valve is open, a quantity of material contained in pressurized can 3 emerges therefrom, and is propelled through shaft tube 29 and nozzle tube 31. The material emerging from nozzle tube 31 is deflected by the metallic disk 39, and is heated thereby.

The propulsion gas including air drawn by the emerging material and the more volatile components of the material or agent contained in can 3 escape instantly, and under pressure from the can, through the holes 40 of heated disk 39, and spread out into the atmosphere surrounding the apparatus. The less volatile components are deposited on disk 39, which is slightly absorbant with respect to these components. The deposited components evaporate then gradually after interruption of the actuation of the can valve, the supply of electrical current to the heater element 35 being continued as long as the apparatus is used. These gradually evaporating components escape to the environment, their flow being enhanced by the natural air flow entering into the apparatus through the bottom openings 4 of case 1 and the slits 7 in top case 5, and leaving the apparatus through the holes 40 of heated disk 39.

As residues from the material heated and dispersed by the heated disk 39 may permanently adhere to that disk, and as such residues, after prolonged use of the apparatus, may represent some inconveniences, especially if the residues comprise toxic components, a system of replacement of disk 39 at the time when a fresh can 3 has to be substituted for an empty can, is provided. According to FIG. 4, a replacement package 41 not only comprises a pressurized full can 3, but also the metallic plate 38 and the metallic disk 39 shown in FIG. 2. Plate 38 is plugged on the outlet portion of can 3 with its sleeve-shaped protrusion, and disk 39 is laid onto plate 38 as for use in the apparatus of FIG. 2. A plastic or metallic cap 42 fits over the top portion of can 3 including plate 38 and disk 39 to prevent their loss or damage.

In use, top cap 5 (FIG. 2) is removed from case 1. Disk 39 and plate 38 are also removed for safe disposal. Latches 16 are then rotated to free the empty can 3 which is also removed from case 1. After removal of cap 42 from package 41 (FIG. 4), and after removal of plate 38 and disk 39 from can 3 in package 41, that can is inserted in case 1 and secured therein by rotating the latches 16 in the opposite sense. Fresh plate 38 and disk 39 are then put on the heating device 34 (FIG. 2), and top cap 5 is again put on case 1. After reconnecting cord 11 (FIG. 1) to the a.c. mains, the apparatus is again ready to operate according to the program selected by means of selector switch 9, pilot lamp 10 indicating normal operation. In case it should be desired to spray only the material of can 3, but not to heat it, metal plate 38 and metal disk 39 simply are not fitted to the heating device 34 shown in FIG. 2.

The material contained in can 3 may be either a liquid material or a solid material in the form of a powder or grains. Can 3 may also have another type of valve which comprises a short piece of tube protruding from the can. In that case, plunger 28 will be adapted to attack the piece of tube forming part of the can valve. Moreover, can 3 need not be pressurized. Instead, a pump such as known from manually actuated sprayer devices can be arranged in case 1 above the opening of a pressureless container or can inserted in case 1, the pump then being actuated by the solenoid 21, 22.

The present apparatus has the advantage that due to the heating of the material from can 3, a higher quantity of agents is evaporated, and a higher volume of atmosphere is treated with less material. The effectiveness of the apparatus does not depend on the height above sea-level of the place of its use. As the apparatus itself does not include any valve, a common source of trouble is absent.

FIGS. 5 to 8 show preferred embodiments of the control circuit lodged in box 2 (FIG. 2), preferably on a printed circuit board. These embodiments are entirely solid state and perform the following functions:
  (a) They control the temperature of the heating device 34 (FIG. 2) and, consequently, that of the heated metal disk 39;
  (b) They provide for selectable time intervals between successive excitation pulses supplied to solenoid coil 22; and
  (c) They provide for various lengths of the pulses supplied to solenoid coil 22, and thus for various quantities of material supplied to the heating device 34 and the environment at each excitation pulse.

Figure 5:
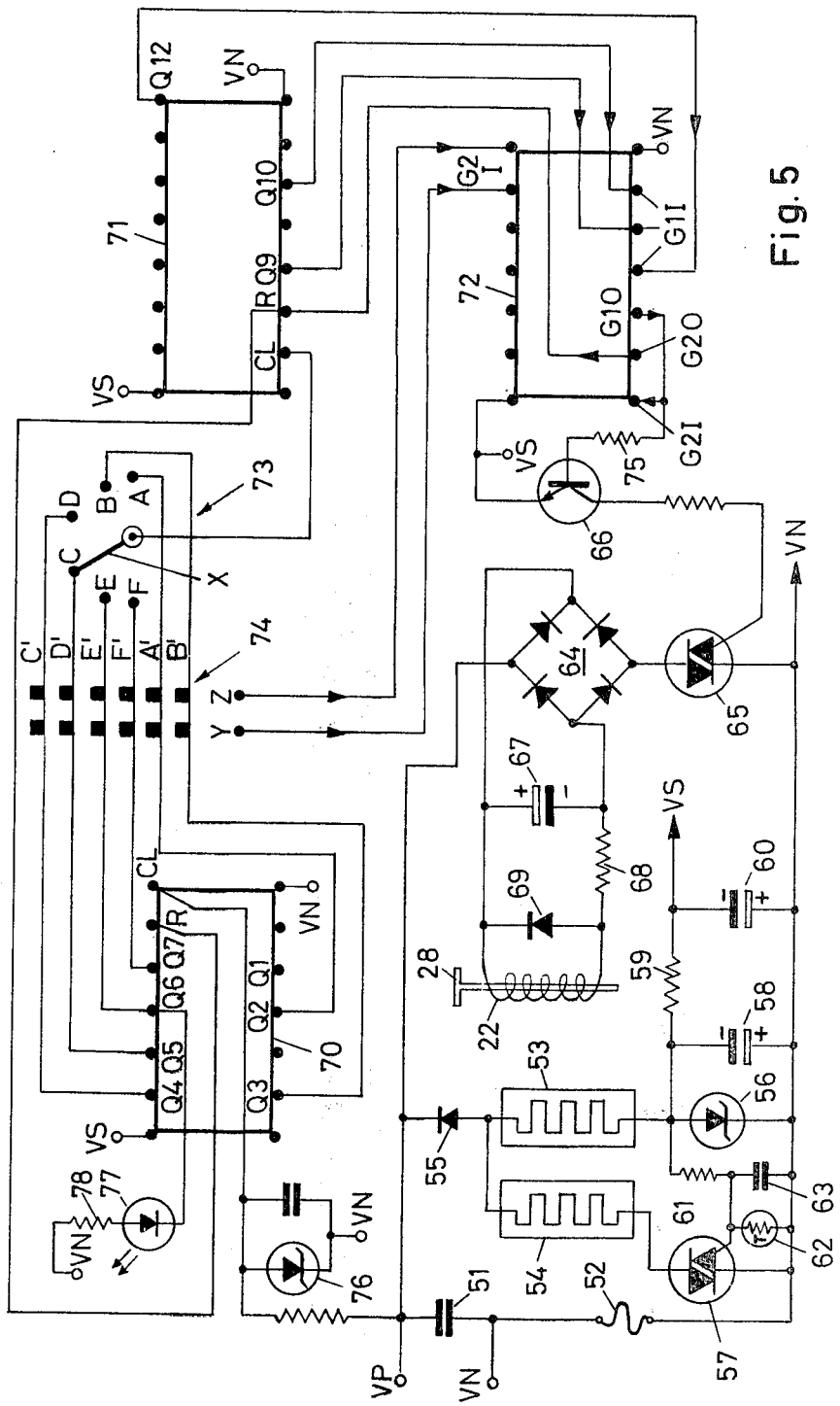
FIG. 5 shows a schematic diagram of a control circuit of the apparatus of FIG. 1 in a form adapted to be used with a mains frequency of 50 Hz.

FIG. 5 shows two input terminals VP and VN which are connected to the phase and neutral leads of an a.c. mains having a voltage of 220 volts and a frequency of 50 Hz. Terminals VP and VN are bridged by a noise suppressor capacitor 51. One of the mains leads, in the embodiment shown the neutral lead, also serves as a common ground for the control circuit. The common ground, connected to terminal VN via a fuse 52, is also designated by VN.

The heating device of the embodiment of FIG. 5 has two resistive heater elements 53 and 54, respectively, which correspond to heater element 35 shown in FIG. 2. Both heater elements 53 and 54 are connected to phase terminal VP via a rectifier 55. To close the respective current loops, heater element 53 is connected to neutral terminal VN through a zener diode 56, and heater element 54 is connected to neutral terminal VN through a triac (or thyristor) semiconductor switch 57. Therefore, current flows constantly in heater element 53 while the current flow in heater element 54 is switched on and off by triac switch 57.

The voltage at zener diode 56 is constant due to a storage capacitor 58. Zener diode 56 is selected to have a zener voltage of 6 volts, for example. The constant voltage is further filtered by a series resistor 59 and a further capacitor 60 for supplying a constant negative d.c. supply voltage VS to several circuit components described below.

The d.c. voltage at zener diode 56 is further used for controlling triac switch 57. A gate of triac switch 57 is connected to zener diode 56 via a resistor 61, and to the common ground VN via a temperature-sensitive resistor 62. Temperature-sensitive resistor 62 is in thermal contact with heating device 34 shown in FIG. 2. Resistor 61 has the dual purpose of a dropping resistor to temperature-sensitive resistor 62 and as a filter resistor, the filter action being completed by a capacitor 63. It is apparent that the series combination of resistors 61 and 62 provides for a temperature-sensitive voltage divider supplying a gate voltage to triac 57 in response to the temperature sensed at heating device 34, thus switching on triac 57 at relatively low temperatures and switching off triac 57 at relatively high temperatures to hold the temperature of heating device 34 substantially constant.

Current supply to solenoid coil 22 actuating plunger 28 is achieved from the a.c. mains terminals VP and VN by means of the series combination of a rectifier bridge 64 and a further triac switch 65, the latter being controlled through a transistor 66. Rectifier bridge 64 provides a d.c. current to solenoid coil 22 for half-waves of both polarities of the mains voltage when triac switch 65 is switched on by the control voltage or current supplied from transistor 66. A storage capacitor 67 smooths the pulsating d.c. current from rectifier bridge 64. A series resistor 68 limits the current supplied to solenoid coil 22, and a back-connected diode 69 keeps reverse current away from coil 22.

Timing signals for transistor 66 which, therefore, determine both the intervals between successive periods of current flow through solenoid coil 22 and the length of such periods are derived from the a.c. mains voltage by means of two pulse-counting integrated circuits 70 and 71, respectively, and a multiple-gate integrated circuit 72. Selector means 73 and 74 offer the feature of selecting the lengths of said intervals and periods, respectively.

Integrated-circuit 70 is a counter having seven binary counting stages such as a CMOS-type integrated circuit commercially available under the type number 4024. Integrated circuit 70 has a clock terminal CL, a reset terminal R, two terminals for connection to the supply voltage VS, VN, and an output terminal Q1 ... Q7 of each binary counting stage. The mains voltage having a frequency of 50 Hz is supplied to the clock input terminal CL via a series resistor, connected to a limiting and clipping zener diode 76 having a zener voltage of 6 volts. Thus, the output pulses at terminal Q1 have a recurrence frequency of 25 Hz (one half of 50 Hz), those at terminal Q2 a recurrence frequency of 12.5 Hz (one fourth of 50 Hz), those at terminal Q3 a recurrence frequency of 6.25 Hz (one eigth of 50 Hz), and so on. Terminal Q6 delivering pulses with a recurrence frequency of 50 Hz divided by $2^6$, i.e., one pulse each 1.25 seconds, is connected to a light-emitting diode 77 which is connected to common ground VN via a resistor 78, and which forms the pilot lamp 10 in FIG. 1.

The output terminals Q2 ... Q7 of integrated-circuit counter 70 are individually connected to switch terminals A ... F, respectively of selector means 73 which is a six-position one-pole selector switch having a movable contact arm X. The connection lines between the output terminals Q2 ... Q7 and the switch terminals A ... F are also provided with further terminals, a pair of terminals A' ... F' being in permanent contact with a respective one of the connection lines. A further pair of terminals Y and Z may be connected to the pairs of terminals A' ... F' in a general manner, i.e., each terminal Y and Z may be individually connected to any terminal of the pairs A' ... F' to form the selector means 74. Preferably, the terminals A' ... F', Y and Z of selector means 74 are arranged and connected, respectively, on a printed-circuit board with all remaining electronic components shown in FIG. 5. Selector means 73 corresponds to the selector switch 9 of FIG. 1 which may be actuated by the user of the present apparatus.

Movable contact arm X of selector means 73 is connected to the clock input terminal CL of the second integrated circuit 71 which also is a multiple-stage binary counter having a total of fourteen binary counting stages. Preferably, integrated circuit 71 is a CMOS-type integrated circuit commercially available under the type number 4020. Only output terminals Q9, Q10 and Q12 supplying counting rates of $2^9$, $2^{10}$ and $2^{12}$, respectively, are indicated in FIG. 5 as only these counter outputs are used in the present embodiment.

Figure 6:
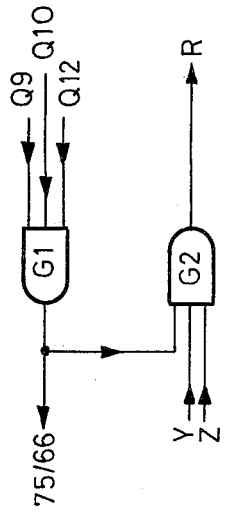
FIG. 6 shows an equivalent diagram of a time interval and pulse length determining portion of the control circuit of FIG. 5.

The third integrated circuit 72 comprises three separate AND-gates, two of which are used in the embodiment of FIG. 5. Such integrated circuit is commercially available under the type number 4073. Each AND-gate G1 and G2 has three input terminals G1I and G2I, respectively, and one output terminal G1O and G2O, respectively. The three input terminals G1I of the first AND-gate G1 are connected to terminals Q9, Q10 and Q12, respectively, of the integrated-circuit counter 71. The output terminal G1O of AND-gate G1 is connected to the base of transistor 66 through a resistor. Two input terminals G2I of the second AND-gate G2 are connected to the terminals Y and Z, respectively, of selector means 74. The third input terminal G2I is connected to the output terminal G1O of the first AND-gate G1. The output terminal G2O of the second AND-gate G2 forms the source of a reset signal supplied to the reset terminals R of integrated-circuit counters 71 and 70. A conventional schematic diagram of the AND-gates of integrated circuit 72 as connected according to FIG. 5 is represented in FIG. 6.

The operation of the time control circuit in FIG. 5 is as follows. If a pulse signal having a period length p is applied to the clock input terminal CL of integrated-circuit counter 71, the pulse signals at the terminals Q9, Q10 and Q12 will have period lengths of p·$2^9$, p·$2^{10}$ and p·$2^{12}$, respectively, i.e., p·512, p·1024 and p·4096, respectively. Therefore, a signal will appear at the output of AND-gate G1 after a time interval corresponding to the sum of the above-mentioned period lengths, i.e., after a time interval of p·5632. If now movable contact arm X of selector means 73 is in position A, the period length of the pulse signal supplied to terminal CL of integrated-circuit counter 71 is 40 milliseconds in view of the positively and negatively going 50 Hz-input signal supplied to input terminal CL of integrated-circuit counter 70, and the connection between arm X and output terminal Q2 in position A. Therefore, an output signal appears at AND-gate G1, and is supplied to transistor 66, after an interval of 40·5632 milliseconds or approximately 225 seconds or $3\frac{3}{4}$ minutes. If movable contact arm X is in position B, the interval will have a length of $7\frac{1}{2}$ minutes. Eventually, if arm X is in position F, the interval will have a length of 2 hours. At the end of the interval selected by the position of the movable contact arm X when an output signal appears at AND-gate G1 and transistor 66 is controlled into conduction, triac switch 65 will be switched on, and a d.c. current will flow through solenoid coil 22, and thereby open the valve of can 3.

The determination of the duration of current flow through solenoid coil 22, i.e., the determination of the instant of resetting the integrated-circuit counters 70 and 71 to start a new timing interval is obtained through the action of AND-gate G2. Whenever signals on all three inputs G2I of AND-gate G2 are present, AND-gate G2 will deliver an output signal which is used as a reset signal supplied to reset terminals R of integrated-circuit counters 70 and 71. Such state at the inputs of AND-gate G2 occurs when there is an output signal at AND-gate G1 and when an interval corresponding to the sum of period length of the pulse signals appearing at those terminals A' . . . F' to which the terminals Y and Z, respectively, are connected, has lapsed. As the pulse signals from output terminals Q2 . . . Q7 of integrated-circuit counter 70 have period lengths between 0.08 seconds and 2.56 seconds, the following table can be drawn for all possible connections of the terminals Y and Z with the terminals A' . . . F'.

TABLE (Values in seconds)

|  |  | ← Y → |  |  |  |  |  |
|---|---|---|---|---|---|---|---|
|  |  | A' | B' | C' | D' | E' | F' |
| ↑ | A' | 0.08 | 0.24 | 0.4 | 0.72 | 1.36 | 2.64 |
|  | B' |  | 0.16 | 0.48 | 0.8 | 1.44 | 2.72 |
| Z | C' |  |  | 0.32 | 0.96 | 1.6 | 2.88 |
| ↓ | D' |  |  |  | 0.64 | 1.92 | 3.2 |
|  | E' |  |  |  |  | 1.28 | 3.84 |
|  | F' |  |  |  |  |  | 2.56 |

From the above table, it is apparent that the length of the period during which solenoid coil 22 is excited and the valve of can 3 is opened to release material contained therein, may be selected, in the present embodiment shown in FIG. 5, between a minimum of 0.08 seconds and a maximum of 3.84 seconds. Normally, however, a specific period length will be selected and fixed by solid connections between terminals Y, Z and one of the terminals A' . . . F', respectively, in consideration of the structure of can 3 and its valve, of the nature of the material to be dispensed, and of other parameters. Contrary to such semi-permanent presetting of selector means 74, the selector means 73 may still be actuated by the user.

Figure 8:
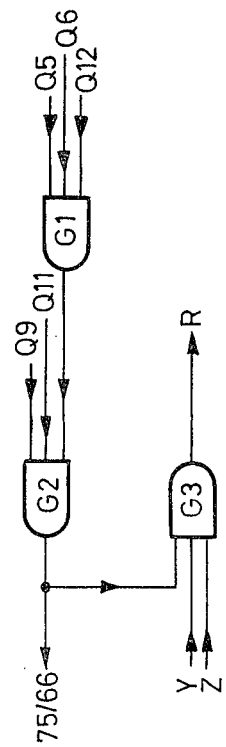
FIG. 8 shows an equivalent diagram of a time interval and pulse length determining portion of the partial control circuit of FIG. 7.
Figure 7:
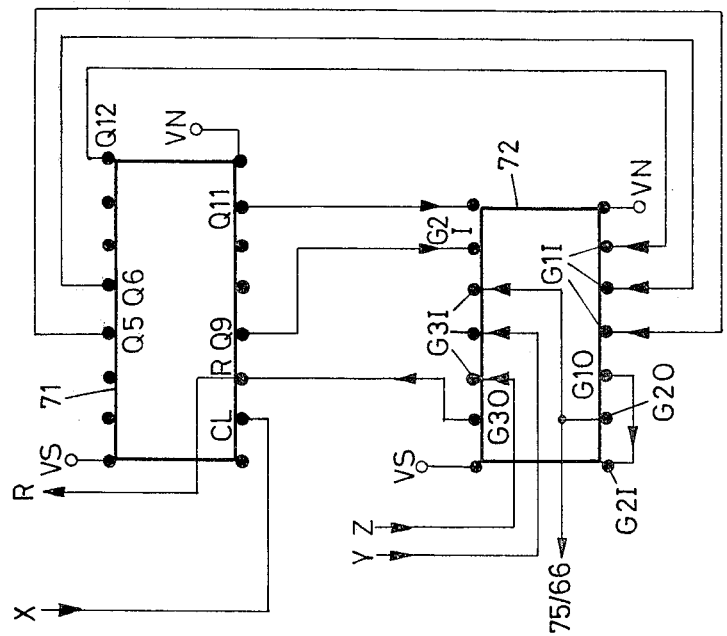
FIG. 7 shows a portion of the control circuit of FIG. 5 in a form adapted to be used with a mains frequency of 60 Hz.

If the a.c. mains frequency is 60 Hz instead of 50 Hz, and if the same intervals of subsequent excitation of solenoid coil 22 as above are desired in the different positions of selector means 73, a different wiring of the connections between integrated circuits 71 and 72 has to be made as shown in FIGS. 7 and 8. In that case, the output terminals Q5, Q6, Q9, Q11 and Q12 of integrated-circuit counter 71, and all three AND-gates G1, G2 and G3 contained in integrated circuit 72 are used. As shown, the three input terminals G1I of AND-gate G1 are connected, respectively, to the output terminals Q5, Q6 and Q12. Two input terminals G2I of AND-gate G2 are connected, respectively, to the output terminals Q9 and Q11. The third input terminal G2I of AND-gate G2 is connected to the output terminal G1O of AND-gate G1. The output terminal G2O of AND-gate G2 is connected to resistor 75 and, therethrough, to the base of transistor 66. Two input terminals G3I of AND-gate G3 are connected, respectively, to the terminals Y and Z of selector means 74 shown in FIG. 5. The third input terminal G3I of AND-gate G3 is connected to the output terminal G2O of AND-gate G2. The output terminal G3O of AND-gate G3 is connected to the reset terminals R of integrated-circuit counters 71 and 70 (FIGS. 7 and 5). Pulses are supplied to the clock input terminal CL of integrated-circuit counter 71 from the movable contact arm X of selector means 73 as before in FIG. 5.

In a similar manner as before, it can be shown that a signal will appear at the output of AND-gate 2 after a time interval corresponding to the sum of the period lengths at the output terminals Q5, Q6, Q9, Q11 and Q12, i.e., after a time interval of p·6752. With movable contact arm X in position A, a signal having a period length p of 33.33 milliseconds will be supplied to input terminal CL of integrated-circuit counter 71. Therefore, an output signal appears at AND-gate G2, and is supplied to transistor 66, after an interval of 33.33·6752 milliseconds, which again is after 225 seconds or 3¾ minutes.

The duration of current flow through solenoid coil 22, i.e., the instant of the generation of a reset signal in the case of an a.c. mains frequency of 60 Hz will be slightly different from the values shown in the preceding table.

It is to be understood that the foregoing, as well as the accompanying drawings, relates to embodiments given by way of example, not by way of limitation. Numerous other embodiments and variants are possible, without departing from the spirit and scope of the invention, its scope being defined by the appended claims.

I claim:

1. An apparatus for electrically dispensing a material to the atmosphere by evaporation of said material, comprising a case for receiving a container holding said material, locking means for releasably securing said container in said case, an electrically controlled actuator assembly in said case adapted to be releasably coupled to said container for causing a quantity of said material to emerge from said container at selectable time intervals and during preset periods, said actuator assembly comprising a ring-shaped solenoid surrounding a plunger connectable to an outlet of said container, and electrical control means connected to said solenoid of said actuator assembly for supplying energizing current to said solenoid including means for selecting said time intervals and means for presetting said periods, characterized in that said plunger (28) has an axial bore receiving a shaft tube (29), one end of which is provided with a nozzle tube (31), and in that there is provided an electrical heating assembly (34,39) comprising an electrically heated body (34) having a bore (37) coaxially aligned with said nozzle tube (31), a heating surface substantially perpendicular to said bore (37) at the side of said body (34) away from said nozzle tube (31), and a plate (39) releasably resting on said heating surface in thermal contact therewith and at least partially covering said bore (37), said plate (39) having a plurality of holes (40) therein.

2. An apparatus according to claim 1, characterized in that said locking means comprise at least one latch (16) pivotally mounted on said case (1).

3. An apparatus according to claim 1 or 2, characterized in that said container is a pressurized can (3) having an axially movable outlet valve.

4. An apparatus according to claim 3, characterized in that said shaft tube (29) is axially movable in said plunger and has one end resting on said outlet valve in said can (3), an engaging element (30) being fixed on said shaft tube (29) for receiving a thrust from said plunger.

5. An apparatus according to claim 4, characterized in that said electrically heated body (34) is ring-shaped and rests on a heat insulating plate (25) mounted on said solenoid (21,22), said plate in thermal contact with said body being a perforated disk (39).

6. An apparatus according to claim 1, characterized by a top cap (5) fitted to said case (1) for covering said actuator assembly (21,22,29), said top cap having a mesh portion (6) surrounding said heating assembly (34,39).

7. An apparatus according to claim 13, characterized in that said electrical control means comprise controllable switch means (65) for supplying energizing current to said actuator assembly (21,22), timing means (70,71) for deriving time-related signals, and selector means (73,74,72) for selecting specific control signals from said time-related signals, said selected control signals being supplied to said controllable switch means, and said selected control signals determining both the length of time intervals between successive periods of flow of current in said solenoid and also the duration of each of said periods of flow of current.

8. An apparatus according to claim 7, characterized in that said timing means include first and second counters (70,71) each comprising an input (CL), a plurality of binary counting stages having a respective output (Q1 . . . Q12), the input of said first counter (70) being connected to an alternating voltage source (VP,VN), the input of said second counter (71) being selectively connected to one of the outputs of said first counter through a selector switch (73), and at least part of the outputs of said second counter being connected to gate means (72) for deriving said control signal determining the length of said time intervals.

9. An apparatus according to claim 8, characterized by further selector means (74) selectively connecting two of the outputs of said first counter (70) to further gate means (72) for deriving said control signal determining the duration of said periods, and for generating a reset signal supplied to said first and second counters (70,71).

10. An apparatus according to claim 1, characterized in that said electrical control means including said electronic circuit means is located in a housing (2) attached to said case (1) comprising said container (3).

11. The apparatus of claim 1 including a replacement package comprising a container (3) holding material to be evaporated, a perforated disk (39) for contact with the material emerging in said apparatus from said container, and a cap (42) fitted to said container and adapted to retain said disk on said container.

12. A replacement package for an apparatus for electrically dispensing a material to the atmosphere by evaporation of said material, comprising a case for receiving a container holding said material, locking means for releasably securing said container in said case, an electrically controlled actuator assembly in said case adapted to be releasably coupled to said container for causing a quantity of said material to emerge from said container at selectable time intervals and during preset periods, said actuator assembly comprising a ring-shaped solenoid surrounding a plunger connectable to an outlet of said container, and electrical control means connected to said solenoid of said actuator assembly for supplying energizing current to said solenoid including means for selecting said time intervals and means for presetting said periods, characterized in that said plunger (28) has an axial bore receiving a shaft tube (29), one end of which is provided with a nozzle tube (31), and in that there is provided an electrical heating assembly (34,39) comprising an electrically heated body (34) having a bore (37) coaxially aligned with said nozzle tube (31), a heating surface substantially perpendicular to said bore (37) at the side of said body (34) away from said nozzle tube (31), and a plate (39) releasably resting on said heating surface in thermal contact therewith and at least partially covering said bore (37), said plate (39) having a plurality of holes (40) therein; said replacement package comprising:

a container (3) holding material to be evaporated, and a cap (42) fitted to said container and adapted to retain said disk on said container.

* * * * *